United States Patent [19]

Nishino et al.

[11] 4,419,302
[45] Dec. 6, 1983

[54] STEAM GENERATOR

[75] Inventors: Atsushi Nishino, Neyagawa; Tadashi Suzuki, Katano; Kazunori Sonetaka, Hirakata, all of Japan

[73] Assignee: Matsushita Electric Industrial Company, Limited, Osaka, Japan

[21] Appl. No.: 269,021

[22] PCT Filed: Sep. 26, 1980

[86] PCT No.: PCT/JP80/00223
§ 371 Date: May 28, 1981
§ 102(e) Date: May 28, 1981

[87] PCT Pub. No.: WO81/00903
PCT Pub. Date: Apr. 2, 1981

[30] Foreign Application Priority Data

Sep. 29, 1979 [JP] Japan ................................ 54-125578
Sep. 29, 1979 [JP] Japan ................................ 54-125579
Sep. 5, 1980 [JP] Japan ................................ 55-123809
Sep. 11, 1980 [JP] Japan ................................ 55-127450

[51] Int. Cl.³ ............................................. B01F 3/04
[52] U.S. Cl. ........................................ 261/142; 122/487;
128/204.13; 128/204.17; 219/274; 261/104;
261/154; 261/DIG. 65; 422/125

[58] Field of Search ............... 261/104, 142, 153, 107,
261/154, DIG. 65, 78 A; 128/200.11, 204.17,
204.13; 219/271–276; 122/487; 422/125

[56] References Cited

U.S. PATENT DOCUMENTS

| | | | |
|---|---|---|---|
| 3,092,708 | 6/1963 | Walther | 261/142 X |
| 3,178,159 | 4/1965 | Johnson | 261/142 X |
| 3,234,357 | 2/1966 | Seuthe | 261/142 X |
| 3,355,155 | 11/1967 | Heltzen et al. | 261/142 X |
| 3,672,568 | 6/1972 | Foote | 261/142 X |
| 3,873,806 | 3/1975 | Schossow | 261/142 X |
| 3,891,826 | 6/1975 | Seuthe et al. | 261/142 X |
| 4,225,542 | 9/1980 | Wall et al. | 261/142 |
| 4,288,396 | 9/1981 | Ottestad | 261/142 X |

Primary Examiner—Richard L. Chiesa
Attorney, Agent, or Firm—Lowe, King, Price & Becker

[57] ABSTRACT

This invention relates to a steam generator for evaporating from a vaporizing portion (17) thereof a liquid (12) sucked up by means of a liquid sucking-up member (10) to provide a steam generator which is capable of vaporizing a liquid efficiently in a short time by application of heat from a heating unit (13) and air fed from a fan (15).

16 Claims, 16 Drawing Figures

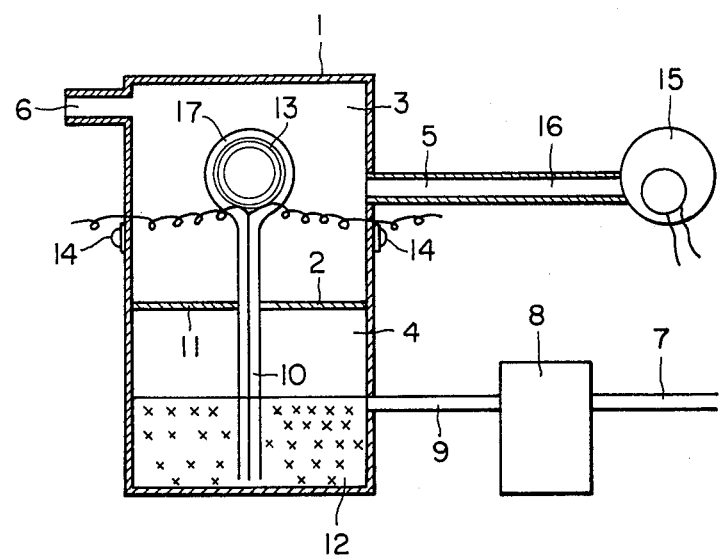
FIG. 1
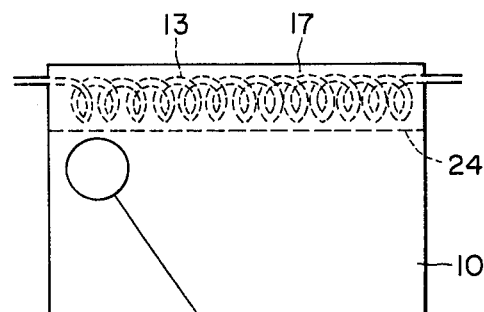
FIG. 2
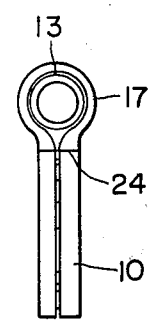
FIG. 3
FIG. 4

STEAM GENERATOR

TECHNICAL FIELD

This invention relates generally to steam generators for use in humidifiers, steam inhalers or the like which are capable of efficiently generating steam within a short time interval.

BACKGROUND ART

In recent years, there have been developed a number of steam generators such as humidifiers, steam irons, steam inhalers, all of which have become popular in the market.

In particular, humidifiers and inhalers have been favorably noticed. Inhalers are effective as a measure for bronchitic or asthmatic patients, so that many related articles have been recently developed. However, most known inhalers are arranged such that 300–400 ml of water in a container is heated by means of an electric heater to generate steam and a saline solution or an adrenaline solution is sprayed entrained with the steam by application of a spraying principle using the pressure of the generated steam. For generators of this type, it takes approximately 7 minutes during the summer season and 10–15 minutes in the winter before steam is generated after introduction of water. Thus, most of the generators, in addition to requiring a relatively long time duration before steam generation, also involve difficulty in controlling the temperature of steam and no steam generation occurs unless a certain level of water is provided in spite of their use for a short time, and are poor in economy from a viewpoint of energy saving.

The humidifier is also becoming an important electric article in view of the growing demand for air conditioning coolers and the FF-type heating apparatus as a preventive measure against dryness of the air when using air conditioning coolers in the summer season or as a measure of humidification required when the FF type heaters are used in the winter season.

In principle, humidifiers are divided into two groups, ultrasonic and heating types. The heating type humidifier is scarcely employed since it requires a long time before steam is generated (as is the case with inhalers), resulting in poor economy from the standpoint of energy costs. On the other hand, the ultrasonic system is employed and since it generates water droplets (not steam) having a size of 5–30 μm, it appears visually that steam generated simultaneously with the electric source being turned on; howwever, it actually takes a long time before the water droplets are vaporized into steam. In addition, fine water droplets (5–30 μm) generated from the ultrasonic humidifier does not reach the lung by adsorption with organs, and thus the ultrasonic humidifier is not so favored from a standpoint of health. As a matter of course, there has been heretofore made an effort to improve ultrasonic generator elements in order to make finer the water droplets of the ultrasonic humidifier. To obtain finer water particles requires greater amounts of electric energy or involves greater levels of noise. As a consequence, the humidifiers which have been practically utilized from a view point of their commercial value are, in most cases, those in which the size of water droplets is in the range of 5–30 μm, but such size was not satisfactory. That is, it is medically accepted that when taking into account an influence on human body, a particle size of below 1 μm or a steam-like particle size is most ideal.

DISCLOSURE OF THE INVENTION

Accordingly, the present invention contemplates to efficiently generate a necessary amount of steam within a short time.

BRIEF DESCRIPTION OF THE DRAWINGS

FIG. 1 is a front, sectional view of a steam generator showing one embodiment of the invention;

FIG. 2 is a front view of a portion of a liquid sucking-up member of FIG. 1;

FIG. 3 is a side view of the liquid sucking-up member;

FIG. 4 is an enlarged front view of an essential part of the liquid sucking-up member;

and

Figure 16:
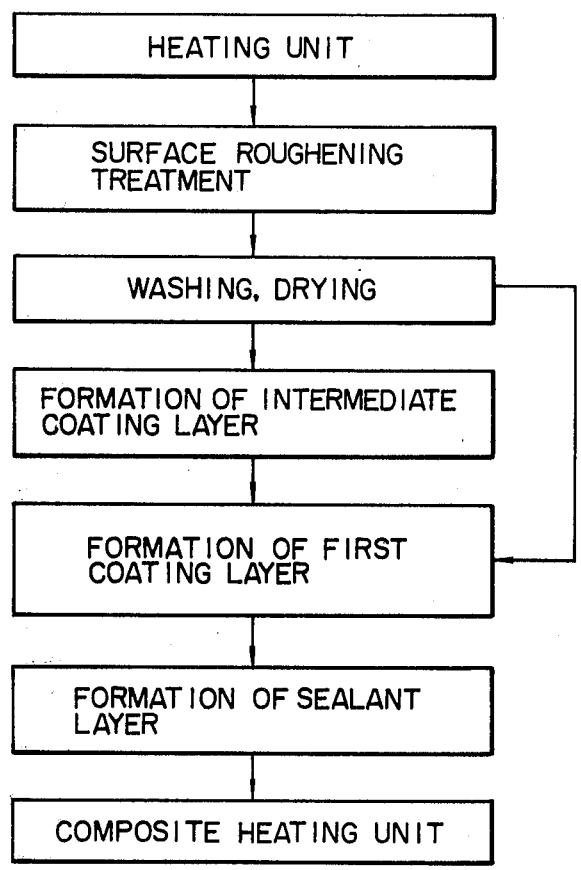

FIG. 16 is a flow chart showing a procedure of making a heating unit.

BEST MODE FOR CARRYING OUT THE INVENTION

In FIGS. 1–4, a container 1 for generating steam is divided through a partition plate 2 into a vaporizing chamber 3 and a liquid storing chamber 4. Vaporizing chamber 3 is, if required, provided with a gas charge port through which a gas is charged and a discharge port 6 through which a vaporized steam is discharged. Liquid from a liquid charge pipe 7 is maintained at a certain level by a liquid leveller 8 and then introduced into liquid storing chamber 4 through a liquid charge pipe 9.

A liquid sucking-up member 10 having capillary action extend into liquid storing chamber 4 and vaporizing chamber 3 through a through-hole 11 provided in partition plate 2.

Liquid sucking-up member 10 is immersed at the lower end thereof in a liquid 12 kept in the liquid storing chamber 4, and at its upper end it extends into the vaporizing chamber 3 and is provided with a heating unit 13. Heating unit 13 generates heat by application of an electric current from terminals 14 where required.

Vaporizing chamber 3 is arranged to be fed with a gas, such as air, when required, by means of a fan 15 causing gas to flow through a gas introduction pipe 16 and gas charge port 5.

The operation of the steam generating unit shown in FIG. 1 is now described by way of example of water vapor generation. Water is fed from a water service pipe or through an electromagnetic valve (for water service) into liquid charge pipe 7 and then stored through the liquid leveller 8 and charge pipe 9 in liquid storing chamber 4 as a liquid 12. This water is then sucked up by means of liquid sucking-up member 10 via its capillary action so that it reaches a vaporizing portion 17 of the liquid sucking-up member. Portion 17 is provided to cover the outer surface of heating unit 13 disposed within vaporizing chamber 3.

The flow rate of air to be fed will accelerate evaporation from member 10, i.e. an increase in flow rate of air results in an increase in an amount of generated steam. The experiment made by the present inventors revealed that the accelerating effect was shown when the flow rate of a gas such as air which passed while being contacted with the liquid sucking-up member 10 on the surface thereof was about 0.1 m/s. It will be noted that the flow rate of 0.1 m/s is determined under conditions of 1 atm., R.H. of 45% and room temperature of 20° C.

As described above, the amount of evaporating steam increases when the flow rate of gas is above 0.1 m/s but optimum conditions are obtained when the flow rate is in the range of 2-3 m/s. It has been found that when the flow rate exceeds 3 m/s, the amount of evaporation does not increase proportionally to the supplied energy involved in the gas.

A relationship between the amount of evaporating water and the supplied electric energy was determined in cases where air was fed into container 1 from charge port 5 and where no gas was charged.

Figure 5:
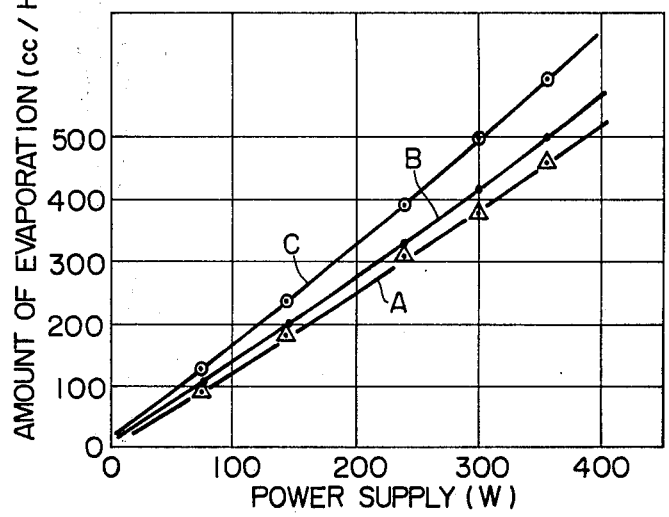
FIG. 5 is a characteristic graph.

FIG. 5 shows the results of the experiment.

The apparatus used for the experiment was the steam generator of the embodiment according to the invention shown in FIG. 1. The experimental conditions are as follows: (A) No air was fed by means of the fan 15; (B) The fan 15 was controlled so that a flow rate of air which flowed in contact with the surface of the liquid sucking-up member 10 was 0.1 m/s; and (C) A flow rate of air was controlled to be 2.5 m/s by a procedure similar to the case of (B).

As is clearly seen from FIG. 5, even though electric power supplied to heating unit 13 is held at the save level, a greater amount of evaporated steam is obtained in the case (B) where air is fed by means of the fan 15 than in the case (A) where no air is fed from the fan 15 and a greater flow rate of air as in (C) results in a much greater amount of evaporated steam.

A feature of the steam generating unit having such an arrangement as shown in FIGS. 1-4 resides in that since it is sufficient to vaporize water alone which has been fed to the vaporizing portion 17 provided around the heating unit 13, a required amount of steam can be fed over a required period of time only 3-5 seconds after application of an electric current to the heating unit 13. Accordingly, it is possible to almost instantaneously generate steam without raising the temperature of the entire amount of water in the container to 100° C. as will be experienced in prior art counterparts. The essential parts of the steam generating unit of the invention will be described in detail.

<KIND OF LIQUID 12>

As liquid 12, there can be used most of various liquids such as water, aqueous solutions, solvents, drugs, kerosene and the like.

<CONSTITUTING MATERIALS FOR CONTAINER 1>

Container 1 can be made of metals, resins, ceramics and the like. In particular, the inner surface of vaporizing chamber 3 and inner surface portion of the partition plate 2 at the side facing vaporizing chamber 3 is preferably either constituted of heat-resistant, heat-insulating or flame-retarding materials or lined. For instance, it is preferable that the container 1 is constituted of a metal and then lined with a flame-retarding resin or enameled.

<LIQUID SUCKING-UP MEMBER 10>

Liquid sucking-up member 10 having a capillary action is desired to have a water suction rate of above 10 mm/sec. This was confirmed by a test in which a fiber constituting the liquid sucking-up member 10 (e.g. a glass fiber) or asbestos fiber was immersed in water colored with a colorant dye, and a height of the water sucked up in 10 seconds was measured.

Most fibrous materials show a rate of above 10 mm/sec., but among foamed materials there are a number of materials whose rate is below 10 mm/10 sec.

A rate greater than 10 mm/10 sec. will make it possible to efficiently generate steam in a required amount. With rates below 10 mm/sec., the heat energy from heating unit 13 may not be satisfactorily utilized, thereby lowering heat efficiency.

The most preferable materials for the liquid sucking-up member include glass fibers, alkali-proof fibers, silica fibers, alumina fibers and the like. The (plain-like thick gause), Calico weave, twill weave and the like of these fibers are most suitable for the purpose of the invention. Other materials including cloth and fabric materials made of flame-retarding fibers such as carbon fibers, asbestos and novolac fibers, metallic fibers and ceramic fibers also satisfy the purpose of the invention but they are slightly inferior in fiber strength, processability, heat resistance and cost to glass fibers. In addition, heat-resistant porous materials and foamed materials are usable but are inferior in processability and sucking-up ability to glass fibers.

Liquid sucking-up member 10 according to the present invention is characterized not only by its high capability of sucking up water using capillary action as described hereinabove, but also by its ability to provide a sterilizing action for preventing propagation of bacteria.

Figure 6:
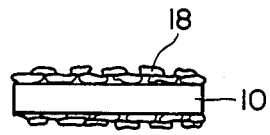
FIG. 6 is an enlarged view of the liquid sucking-up member of FIG. 1.

FIG. 6 shows a liquid sucking-up member 10 having deposited on the surface thereof a bactericide 18 such as, for example, a sparingly soluble silver salt.

Figure 7:
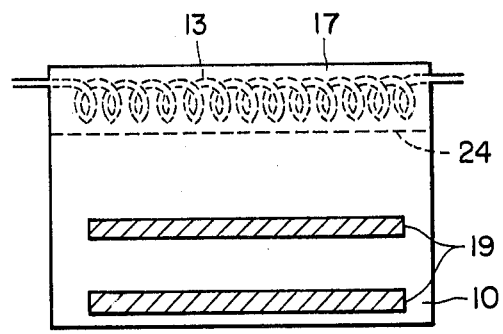
FIG. 7 is a front view of another embodiment of the liquid sucking-up member.
Figure 8:
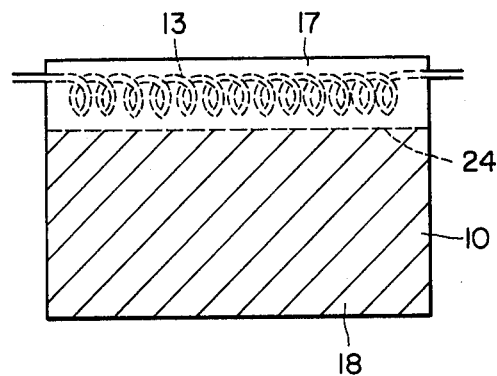
FIG. 8 is a front view of a further embodiment of the liquid sucking-up member.
Figure 9:
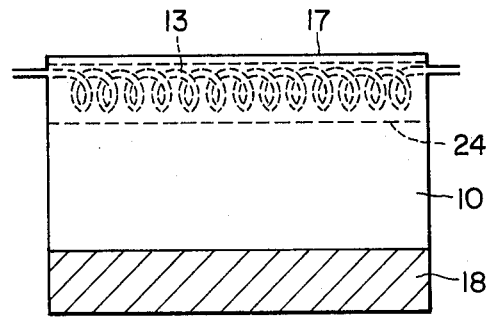
FIG. 9 is still a further embodiment of the liquid sucking-up member.

FIGS. 7-9 show the liquid sucking-up member 10 which has imparted on the surface thereof other arrangements to provide a sterilizing function. FIG. 7 shows a liquid sucking-up member 10 which is disposed with a sterilizing member 19 in the form of a plate or rod made of a sterilizing metal or metal salt such as Cu, Ag, AgCl or the like. Sterilizing member 19 may be formed by depositing a sterilizing metal or metal salt such as, for example, Cu, Ag, AgCl or the like on the surface of a protecting substrate. FIG. 8 shows an arrangement in which a bactericide 18 composed of a sterilizing metal or metal salt is directly deposited on part of the liquid sucking-up member 10. FIG. 9 is similar to FIG. 8 and shows an arrangement in which the liquid sucking-up member 10 is constituted of a porous ceramic which has directly deposited at a lower portion thereof a bactericide 18 made of a sterilizing metal or metal salt.

Most preferable protecting substrates of the sterilizing member 19 are those made of carbon fibers, chemical fibers, glass fibers and the like. Especially suitable chemical fibers are those which are water proof, such as vinylon, nylon and the like. These fibers are shaped in the form of threads, clothes, and non-woven fabrics and applied as the protecting substrate for sterilizing member 19.

Figure 10:
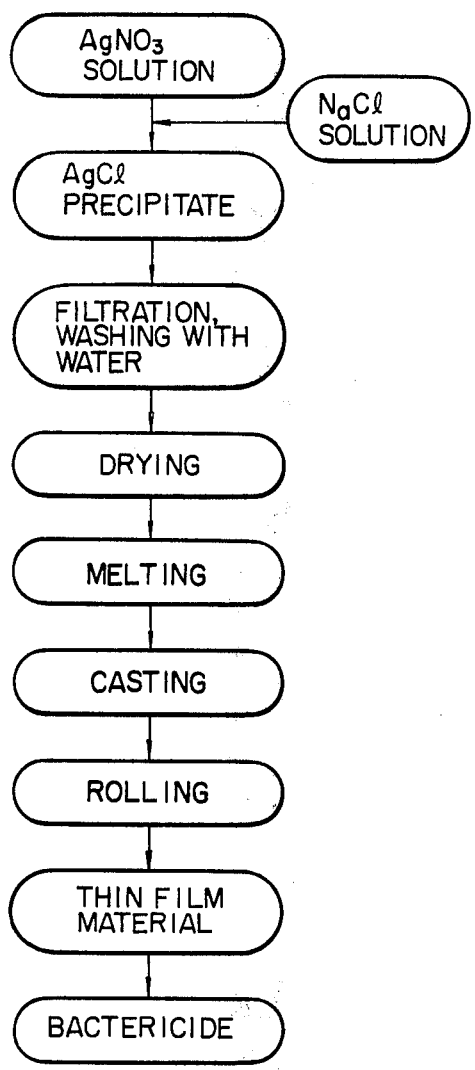
FIG. 10 is a flow chart showing a procedure of making a bactericide.
Figure 11:
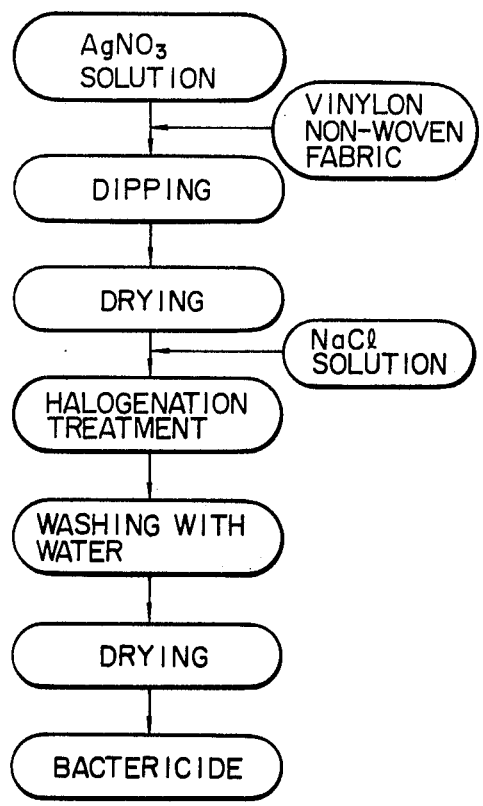
FIG. 11 is a flow chart showing another procedure of making a bactericide.

FIG. 10 and 11 show procedures for making the sterilizing member 19.

That is, FIG. 10 shows a process of making, as the sterilizing member 19, a plate-like band obtained by rolling AgCl and FIG. 11 shows a process of making the sterilizing member 19 by depositing AgCl on the surface of a protecting substrate made of a vinylon non-woven fabric. First, the process shown in FIG. 10 is described in detail. To a AgNO$_3$ solution was added a NaCl solution to deposit AgCl precipitate according to the following reaction formula

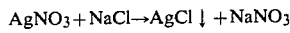

The AgCl precipitate is filtered and washed to remove NaNO$_3$ and NaCl (remaining in excess). Thereafter, the AgCl is dried, melted at temperatures of 480° to 520° C. (melting point 455° C.), and cast in the form of a plate, rod or the like. After cooling, the casting is hot rolled to obtain a sterilizing member 19 in the form of a thin film. The process of FIG. 11 is now described. AgNO$_3$ is uniformly deposited on a protecting substrate such as a vinylon non-woven fabric in a vessel for AgNO$_3$ solution and dried to remove moisture. Then, the AgNO$_3$ is halogenated in a vessel of NaCl solution, washed with water and dried to give a sterilizing member 19.

The sterilizing function is now described. A useful bacteriological inspection for water is expressed in terms of a total number of bacteria in 1 milli-liter of water and completely sterilized water is extremely low in number of bacteria, e.g. the standard for drinking water has been legally decided as below 100 bacteria per milli-liter of water. These bacteria are generically called general bacteria and aside from these bacteria, colitis germs are needed to examine. It is more important to note that there are also present in water molds to be aquatic plants (duckweeds) resembling bacteria.

It can not be said that all of these microorganisms in water are harmful to human body but it is a matter of fact that sterilized water is better than propagated water.

The sterilizing effect of heavy metal ions in water is called Oligodynamic action, meaning a sterilizing effect on microorganisms shown by a small amount of a certain type of metal ions. Stated more specifically mercury, silver, copper and like metals show a strong sterilizing action in their ionic states (Hg$^{++}$, Ag$^+$, Cu$^{++}$). The metallic ions serve to kill microorganisms only in an extremely small amount (10$^{-6}$ M). This action may be called an oligodynamic action.

As the bactericide 18 there may be mentiond metals such as mercury, copper, silver, zinc, lead, iron and the like as mentioned above and their oxides, carbonates, halides, nitrates and the like, of which materials showing a less ill effect are copper, silver, zinc and iron. In particular, copper, silver and their salts are excellent in economy, production process and processability, and also in sterilizing effect. Alternatively, those which are high in safety and show an excellent sterilizing effect even when used in very small amounts include silver or its salts, which show a small solubility in water and are usable over a long time and sufficient to apply in small amounts. The solubilities of silver and silver salts are, for example, as follows: 10$^{-5}$ mol/l for silver chloride, 10$^{-6}$ mol/l for silver bromide, and 10$^{-8}$ mol/l for silver iodide, of which silver chloride is more advantageous in view of sterilizing effect, processability, production process and cost.

<HEATING UNIT 13>

Any heating units which can supply an energy necessary for vaporizing a liquid sucked by the liquid sucking-up member 10 are suitable for the purpose of the invention.

As a heating material, for instance, commercially available heating wires and heating bands made of Ni-Cr, Fe-Cr, Fe-Cr-Al, Fe-Cr-Al-Y, and stainless steel are all usable. Aside from these, heating materials such as PCT heating elements, sheathed heaters, heat pipes, heat conductors, composite heating elements which are obtained by spray coating of electric heating wires with ceramics on the surface thereof such as by a plasma spray coater are usable as the heating unit of the invention. The surface structure of heating unit 13 is now described. The heating unit is mainly made of a usual heating wire and a sheathed heater because of economy and ease in attachment. When the surface is flame spray coated with a metal oxide (or double oxide) 20 by a spray coating means such as a plasma spray coater to shown in FIG. 12, this serves as accelerate vaporization to allow a liquid to be efficiently vaporized. That is, the coating plays an important role in improving the efficiency of contact with the liquid sucking-up member 10, accelerating the introduction of a liquid to the surface of the heating unit 13, serving to accelerate vaporization on the surface of the heating unit 13 as boiling stone, keeping nichrome wires insulated and the like, making it possible to permit the vaporization to proceed efficiently.

Figure 12:
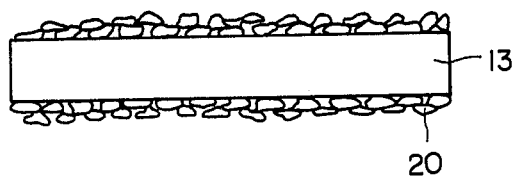
FIG. 12 is an enlarged view of a heating unit.

FIG. 12 shows a first coating layer made of a metal oxide (or metallic double oxide) 20 on the surface of the heating unit 13 made of a heating wire or a resistor. Since the surface temperature of the heating unit 13 used in the present invention is preferred to be in the range of 200°–250° C., its thermal expansion does not prevent metal oxide (or metallic double oxide) 20 such as Al$_2$O$_3$, TiO$_2$ or MgAl$_2$O$_3$ from being directly coated on heating unit 13 by a plasma spraying technique.

Figure 13:
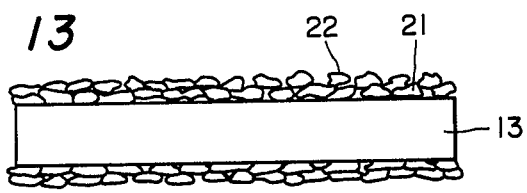
FIG. 13 is an enlarged view of a heating unit.

FIG. 13 shows an arrangement in which a heat-resistant alloy 21 is coated on the surface of heating unit 13 as a first coating layer and then a metal oxide (or metallic double oxide) 22 as a second coating layer is formed thereon. This is because the difference in thermal expansion between the heating unit 13 and the metal oxide (or metalic double oxide) 22 is great, the heat-resistant alloy 21 such as Ni-Cr, Ni-Cr-Al or stainless steel is formed as an intermediate coating layer so that the unit can satisfactorily withstand long periods of use within the heat cycle.

Figure 14:
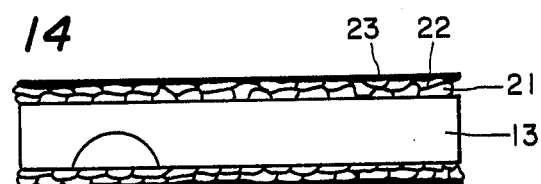
FIG. 14 is an enlarged view of a heating unit.
Figure 15:
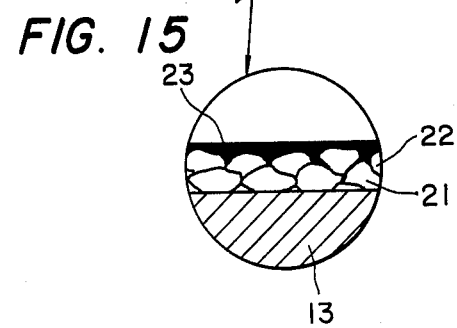
FIG. 15 is an enlarged view of an essential part of FIG. 14.

FIGS. 14 and 15 show an arrangement in which the porous layer of the metal oxide (or metallic double oxide) 22 is treated with a filler 23.

The process of making the heating units of FIGS. 14 and 15 is illustrated with reference to FIG. 16.

<HEATING UNIT 13>

The heating unit 13 is most preferably made of windings of a nichrome wire, iron-chromium wire, Kanthanl alloy wire, Esit (Trade mark) wire, stainless steel wire and the like but other heat sources such as a sheathed heater, PTC ceramister and the like may be used. The present invention is described with reference to a case where usual electric heating wires such as a nichrome wire are applied to heating unit 13.

<SURFACE ROUGHENING TREATMENT>

First, surface of the heating unit 13 is defatted and washed, and then roughened by means of a general abrasive such as $Al_2O_3$, SiC or the like with a grain size of 20–100 mesh under a blast pressure of 3–5 Kg/cm$^2$. It is preferable that heating unit 13 is treated to have an average surface roughness (Ra) of 1–10$\mu$ when measured by the Tallisurf surface roughness tester. Ra values less than 1$\mu$ result in a poor coating efficiency of the metal oxide (or metallic double oxide) 20 and Ra values larger than 10 $\mu$ lead to a difficulty in uniform coating of the metal oxide (or metallic double oxide) 20.

<WASHING DRYING>

Since the heating unit 13 has been deposited with an abrasive or abrasion dust on the surface thereof during the course of the surface roughening step, it is washed with water and then well dried at 100–150 C.

<FORMATION OF FIRST COATING LAYER>

The heating unit 13 used in the present invention is characterized in that a usual heating wire is finely wound in the form of a coil to form a small-size unit of high capacity, thereby making the rise-up time (prepurge) fast. Accordingly, due consideration must be given with respect to electric insulation of the coil. In order to ensure good thermal transmission to water, the surface area of the heating unit 13 should be large. The above requirement can be satisfied by covering the surface with the metal oxide (or metallic double oxide) 20 and thus the intended purpose can be attained.

Examples of material suitable for this purpose include metal oxides 20 such as $Al_2O_3$, $SiO_2$, $Fe_2O_3$, $Y_2O_3$, $TiO_2$, CaO, $B_2O_3$, $Li_2O$, $Cr_2O_3$, $ZrO_2$, MgO, BeO, NiO, $ThO_2$, $HfO_2$, $La_2O_3$, and $CeO_3$ (or spinel type double oxides such as $MgAl_2O_4$, $MnAl_2O_4$, $FeAl_2O_4$, $CoAl_2O_4$, $ZnAl_2O_4$, $MgCr_2O_4$ and the like) and at least one of these compounds is preferably used. Of these, most effective and economical ones are $Al_2O_3$, $TiO_2$, $ZrO_2$, $SiO_2$, and $MgAl_2O_4$.

Methods of coating these materials include arc spray coating, flame spray coating, plasma spray coating, explosion spray coating and the like, of which the plasma spray coating is suitable for the purpose of the invention. In the present invention, the first coating layer was formed by spray coating a metal oxide (or metallic double oxide 20) by using a Model SG-100 plasma spray coating machine of the 80 K.W. type made by Plasma Dyne Co., Ltd., and under conditions of argon gas as an arc gas, helium as an auxiliary gas, an electric current of 1000 A and a voltage of 41 V.

The thickness of the first coating layer was found to be effective at about (10–100)$\mu$.

FORMATION OF FIRST COATING LAYER=FORMATION OF INTERMEDIATE COATING LAYER

A method of forming a coating of a heat-resistant alloy 21 of FIG. 6 is described.

As described hereinbefore, the intermediate coating layer is disposed between heating unit 13 and metal oxide (or metallic double oxide) 22 and should stand stably usable over a long time in the heat cycle of heating unit 13. Most suitable materials as the heat-resistant alloy 21 include Ni-Cr, Ni-Cr-Al, Fe-Cr, Fe-Cr-Al, and Fe-Cr-Ni-Al. It will be noted that the thickness layer of heat-resistant alloy 21 as an intermediate layer was found to be effective at about 5–30$\mu$.

When the intermediate layer of heat-resistant alloy 21 (such Ni-Cr-Al) to be an intermediate coating layer is formed by spray coating on the surface of heating unit 13 (as described above) and then metal oxide 22, such as $TiO_2$, $Al_2O_3$, $SiO_2$, $ZrO_2$ or the like, is formed by spray coating as the first layer, 5–30% of pores are substantially formed in the coating layers, with the result that when immersed in water, the heating unit 13 undergoes oxidation on the surface thereof, showing a varied resistance during long use. This entails a variation of a preset electric power or disconnection in the worst case. To avoid this, a sealant 23 is used. As a result of extensive study for a suitable sealant 23, it was found that both inorganic sealants such as water glass, silica oil, alumina sol, glass powder and the like and organic polymeric sealant such as silicone resin, fluorine resin, heat-resistant paints and the like were effective. Of these organic polymers were preferable and, particularly, a sealant mainly composed of fluorine resins were most effective from standpoint of moisture proof, heat stability, electric insulating property, and corrosion resistivity. The fluorine resin is at least one resin selected from the group consisting of ethylene tetrafluoride resin, propylene tetrafluoride copolymer resin, and ethylene trifluoride resin.

<METHOD OF COUPLING THE HEATING UNIT 13 AND LIQUID SUCKING-UP MATERIAL 10>

In FIGS. 2–4, there is shown a manner of coupling the heating unit 13 and liquid sucking-up member 10. For instance, a plain weave liquid sucking-up member 10 made of a material having a capillary action such as, for example, a glass fiber bundled thread is applied to cover the surface of the heating unit 13 and a seam 24 is sewed in so that the material is allowed to intimately contact heating unit 13. It was confirmed that when water was fully impregnated in the liquid sucking-up member 10 prior to the sewing-in of seam 23, the liquid sucking-up member 10 was stretched to ensure good contact with the heating unit 13.

Examples are now particularly described.

<EXAMPLE 1>

A Ni-Cr wire of 0.4 mm$\phi$ was wound in the form of a coil to have an inner diameter of 5 mm$\phi$, a length of about 4 cm and an entire resistance of 1$\Omega$, thereby forming a heating unit 13. The heating unit 13 was then blasted on the surface thereof and spray coated with powdery alumina having a particle size of 30–100 $\mu$m by a plasma spray coating to provide a 20–30 $\mu$m thick alumina layer in a manner as shown by the metal oxide 21 of FIG. 12. Then, as shown in FIG. 2, heating unit 13 was covered with a liquid sucking-up member made of a thick fabric of glass fiber bundled threads to have a width of 4.5 cm and a height of 8 cm as shown in FIG. 2, and was disposed as shown in FIG. 1.

In this arrangement, the fan of FIG. 1 was stopped and evaporated steam alone was generated. Terminals of a slide auto-transformer were connected to electric terminals 14, through which an electric current was applied at an electric power of 80 W. 5–8 seconds after application, steam was vigorously discharged from the discharge port 6.

To apply the above arrangement as a humidifier, air was fed so that a flow rate of air from the fan 15 was controlled to have 40 cm/sec at the discharge port 6 and the heating unit 13 was applied with an electric power of 30 W. As a result, 3–4 seconds after the application, steam was generated from discharge port 6.

As described above in detail, the steam generating apparatus of this example is compact and lightweight and can generate steam efficiently on application of only a small electric power.

It will be noted that it is very important to constitute the inner surface of the vaporizing chamber 3 with a heat-insulating material. That is, steam generated at the heating unit 13 and the vaporizing portion 17 is again condensed on the inner surface layer of the vaporizing chamber 3. This is why it is important to constitute the inner surface of the vaporizing chamber 3 with an insulating material of small heat capacity.

<EXAMPLE 2>

There were, respectively, used the liquid sucking-up member 10 (glass fiber) used in Example 1 which were subsequently deposited directly with bactericides on the surface thereof (No. 2 and No. 3 of Table 1 shown below), the liquid sucking-up member 10 which were subsequently provided with a plate-like band of a vinylon non-woven cloth deposited with a bactericide on the surface thereof (No. 4 of Table 1 shown below), and the liquid sucking-up member 10 which were subsequently deposited with bactericides (metal plate, metal salt plate) (No. 5, No. 6 of Table 1) to determine the number of propagating bacteria in relation to days of storage of water in the liquid storing chamber 4 of the steam generating unit, i.e. a bactericidal activity, with the results shown in Table 1.

TABLE 1

| Liquid Sucking-up Member | Immediately after Storage of City Water | 1 day (Number) | 3 days | 7 days | 20 days |
|---|---|---|---|---|---|
| free of bactericide | 0 | 4 × 10³ | 5 × 10⁴ | more than 5 × 10⁴ | more than 5 × 10⁴ |
| No. 1 | 0 | 0 | 0 | 0 | 0 |
| No. 2 | 0 | 35 | 10 | 0 | 0 |
| No. 3 | 0 | 0 | 0 | 0 | 0 |
| No. 4 | 0 | 70 | 35 | 6 | 1 |
| No. 5 | 0 | 40 | 25 | 2 | 0 |

As is clearly seen from Table 1, when the liquid sucking-up member is imparted with a bactericidal property as in the present invention, bacteria are prevented from propagating. Wnen the steam generator is applied as a humidifier, almost no bacteria are released in room, thus being very good for health.

EXAMPLE 3

The corrosion resistivity of the heating unit 13 was tested. As test samples, there were provided the heating unit of Example 1 (No. 1 of Table 2 shown below), the heating unit 13 of Example 1 which were subsequently covered with a sealant 23 made mainly of ethylene tetrafluoride resin in a thickness of 20 μm (No. 2 of Table 2), and a coil-like winding of Ni-Cr wire (No. 3 of Table 2).

Those three units were tested.

The experiment was conducted by a salt spray test using a 3% NaCl solution in an atmosphere of 80 C and an increasing amount of oxide 10 days after the test was measured. The results are as shown in Table 2.

TABLE 2

| | Sample | | |
|---|---|---|---|
| | No. 1 | No. 2 | No. 3 |
| amount of oxide (mg/cm²) | 0.05 | 0.00001 | 0.1 |

As will be apparent from the above test results, the heating unit used in the present invention is highly resistant to corrosion. Especially, the heating unit which was filled with the sealant 23 mainly composed of ethylene tetrafluoride resin was very excellent in corrosion resistivity.

<EXAMPLE 4>

In case where the heat generator of the present invention is applied as an inhaler for the respiratory organs, the fan of FIG. 1 is stopped and the power consumption for the heating unit 13 is controlled at 100–150 W, whereupon steam is vigorously jetted out from the discharge port 3. The discharge port 3 is made narrow at the tip thereof so that steam can be jetted out, and in front of the discharge port 3 is provided a thin tube through which a medical solution such as a saline solution or an aqueous adrenaline solution is sucked up.

INDUSTRIAL APPLICATION

As having been described hereinabove, according to the invention, there can be provided a steam generating apparatus which can generate steam efficiently in a short time and is applicable as humidifiers or inhalers.

We claim:

1. A steam generator comprising a container having an upper vaporization chamber and a lower liquid storage chamber, means for partitioning the upper and lower chambers from each other, said vaporization chamber having a gas charge inlet port enabling a gas to be charged into said vaporization chamber and a discharge port for discharging steam generated within said vaporization chamber; a suck-up member disposed to extend into the upper and lower chambers within said container so that one end portion of said suck-up member is immersed in a liquid contained in said lower storage chamber while the other end portion extends into the upper chamber; and heating unit means provided at said other end portion of the suck-up member for heating and vaporizing the liquid absorbed by the suck-up member at the one end portion when it reaches the other end portion of said suck-up member, said heating unit means being in the form of a wire or band and a metal oxide or metallic double oxide layer formed on said wire or band to thereby increase the surface area of the heating unit means in contact with the liquid and improve thermal transmission to vaporize the liquid, said vaporized liquid being entrained by a gas passed through said gas charge port for discharge through said discharge port.

2. A steam generator according to claim 1 further including gas supply means for charging gas into the vaporization chamber to provide a gas flow rate greater than approximately 0.1 m/sec at a point where the gas contacts the suck-up member.

3. A steam generator according to claim 1, wherein said suck-up member is made of an inorganic material having capillary action and selected from the group consisting of glass fibers, alkali-proof fibers, silica fibers and alumina fibers.

4. A steam generator according to claim 3, wherein said inorganic material is in the form of cloths or fabrics.

5. A steam generator according to claim 1, wherein said suck-up member is made of at least one member selected from cloths or fabrics of materials selected from the group consisting of novolac fibers, metallic fibers, ceramic fibers, asbestos and carbon fibers, heat-resistant porous materials and foamed materials.

6. A steam generator according to claim 1, 3, 4 or 5 wherein said suck-up member is constituted of a material having a water suction rate greater than approximately 1.0 mm/sec.

7. A steam generator according to claim 1, wherein said wire or band is made from material selected from the group consisting of Ni-Cr, Fe-Cr, Fe-Cr-Al, Fe-Cr-Al-Y and stainless steel.

8. A steam generator according to claim 7, wherein said metal oxide or metallic double oxide is in the form of a spray-coating on said heating member.

9. A steam generator according to claim 7, further comprising a heat-resistant alloy layer provided between said heating member and said metal oxide or metallic double oxide layer.

10. A steam generator according to claim 7, wherein a sealant layer is formed on said metal oxide or metallic double oxide.

11. A steam generator according to claim 10, wherein said sealant layer is made of a fluorine-containing resin.

12. A steam generator according to claim 11, wherein said fluorine-containing resin includes at least one member selected from the group consisting of ethylene tetrafluoride resin, propylene tetrafluoride copolymer resin and ethylene trifluoride resin.

13. A steam generator according to claim 1, wherein said heating unit means is substantially covered by a portion of said suck-up member extending around the outer surface thereof.

14. The apparatus of claim 1, wherein said such up member includes a wick having capillary action to draw and contain liquid within the vaporization chamber.

15. The apparatus of claim 14, wherein said heating means is disposed within ambient air in the vaporization chamber.

16. The apparatus of claim 1, wherein said upper and lower chambers are substantially entirely partitioned from each other so that the only liquid communicating directly with the vaporization chamber is substantially contained within the suck-up member.

* * * * *